(12) United States Patent
Waterman

(10) Patent No.: US 7,650,657 B2
(45) Date of Patent: Jan. 26, 2010

(54) ANTI-PINCH POINT DEVICES FOR IMAGING PLATFORMS

(75) Inventor: Glenn N. Waterman, Salt Lake City, UT (US)

(73) Assignee: Diacor, Inc., West Valley City, UT (US)

( * ) Notice: Subject to any disclaimer, the term of this patent is extended or adjusted under 35 U.S.C. 154(b) by 0 days.

(21) Appl. No.: 12/101,070

(22) Filed: Apr. 10, 2008

(65) Prior Publication Data

US 2008/0282470 A1    Nov. 20, 2008

Related U.S. Application Data

(60) Provisional application No. 60/922,706, filed on Apr. 10, 2007.

(51) Int. Cl.
*A61G 7/047* (2006.01)
*A61G 7/00* (2006.01)

(52) U.S. Cl. ............................ 5/601; 5/942; 378/209; 600/415

(58) Field of Classification Search ............... 5/601, 5/943; 378/209, 177; 600/415
See application file for complete search history.

(56) References Cited

U.S. PATENT DOCUMENTS

| 4,484,571 A * | 11/1984 | Velazquez ........................ 5/601 |
| 6,907,629 B2 * | 6/2005 | Longton et al. ................ 5/601 |
| 7,257,849 B2 * | 8/2007 | Jahrling ....................... 5/81.1 R |

* cited by examiner

*Primary Examiner*—Alexander Grosz
(74) *Attorney, Agent, or Firm*—TraskBritt

(57) ABSTRACT

Anti-pinch point device for imaging platforms are disclosed. The stationary imaging platform includes a slidable cradle and fixed shroud adjacent both sides of the slidable cradle. An inventive overlay is configured for mounting on a slidable cradle. The inventive overlay moves with the slidable cradle. Elongated perimeter regions of the inventive overlay have elongated ridges formed on the underside thereof adjacent the outer edges of the elongated perimeter regions. The elongated ridges serve to prevent objects from becoming pinched between the inventive overlay and the fixed shroud.

22 Claims, 3 Drawing Sheets

ANTI-PINCH POINT DEVICES FOR IMAGING PLATFORMS

CROSS-REFERENCE TO RELATED APPLICATION

This application claims the benefit of the filing date of U.S. Provisional Patent Application Ser. No. 60/922,706, filed Apr. 10, 2007, for "ANTI-PINCH POINT DEVICES FOR IMAGING PLATFORMS."

TECHNICAL FIELD

The present invention relates generally to medical imaging equipment and, more particularly, to anti-pinch point devices for imaging platforms.

BACKGROUND

FIG. 1 illustrates a conventional computer tomography ("CT") scanner 100. CT scanner 100 includes an x-ray source mounted on a movable ring, gantry 22. Gantry 22 includes an array of x-ray detectors mounted opposite the x-ray source. A patient lies on a cradle 30 that moves through gantry 22. Cradle 30 is supported by stationary imaging platform 40. Gantry 22 is rotated so that the x-ray source and detectors revolve around the patient, while the patient is moving through gantry 22 on cradle 30. Each rotation of gantry 22 generates a two-dimensional x-ray slice of the patient. As the patient moves through gantry 22 the x-ray slice images are stored. The x-ray slices are combined together to form three-dimensional images of the patient and/or a particular organ of the patient.

The top surface of cradle 30 has a semi-tubular shape. In some situations, it is desirable to have a patient lying on a flat surface rather than a semi-tubular surface. FIG. 2 illustrates an overlay 50 designed to lay on a cradle 30. Overlay 50 has a flat upper surface and thus provides a flat upper surface for a patient to lie on. Overlay 50 moves with cradle 30 as cradle 30 moves in and out of gantry 22. Often, stationary imaging platform 40 will include a fixed shroud 45. A problem arises when overlay 50 is placed on cradle 30, a pinch point is formed between overlay 50 and fixed shroud 45. It is possible that a patient's fingers could get caught between the underside of the overlay 50 and fixed shroud 45 as overlay 50 is moving in or out of gantry 22.

FIG. 3 illustrates one approach to solving this problem. Foam strips 60 are placed lengthwise along the underside of overlay 50 adjacent the edges to reduce the space between fixed shroud 45 and overlay 50. The reduction in space is designed to prevent objects from becoming pinched between fixed shroud 45 and overlay 50. One problem with this approach is that foam is not very resilient. The foam can be easily torn, distorted, or lose its adhesion to overlay 50. An additional problem with this approach is that the foam is difficult to clean. Often during a CT scan a variety of fluids may be present. For example, a patient may be receiving intravenous fluids. Or, a patient may be receiving iodine or a radioactive dye to assist with imaging during the CT scan. These fluids could be spilled on overlay 50, and therefore on foam strips 60. Additionally, even if no external fluids are present, an ill patient may vomit or urinate during the CT scan. Foam strips 60 would absorb these fluids. It is difficult to sufficiently sterilize foam strips 60.

What is needed is a different solution to address the pinch point that forms between fixed shroud 45 and overlay 50.

BRIEF SUMMARY OF THE INVENTION

Embodiments of the invention include an elongated overlay having a width, length, and structural integrity to support a human body. The elongated overlay may include a middle region and two elongated perimeter regions formed on opposing edges of the middle region. The elongated perimeter regions may be thinner than the middle region. Elongated ridges may be located on the underside of the elongated perimeter regions adjacent outer edges of the elongated perimeter regions. The underside of the elongated overlay is sized and adapted to interact with another structure.

Embodiments of the invention include an imaging platform. The imaging platform may include a frame structure sized and configured to support a slidable cradle. The slidable cradle may be configured for slidable attachment to the frame structure. A fixed shroud may be attached to the frame structure. The fixed shroud may be formed adjacent opposing sides of the slidable cradle. The imaging platform may include an overlay, sized and adapted to support a human body. The overlay may be detachably mounted on the slidable cradle. The overlay may include elongated perimeter regions having elongated ridges formed on the underside thereof. The lower surface of a middle region of the overlay may be configured to mate with the semi-tubular top surface of the slidable cradle.

Embodiments of the invention may include an imaging device. The imaging device may include a rotatable gantry and a platform. The platform may include a frame structure. The platform may also include an overlay, sized and adapted to support a human body, detachably mounted on an elongated slidable cradle. The overlay and the elongated slidable cradle may be configured to slide in and out of the rotatable gantry via the frame structure. The elongated ridges may be formed on underlying elongated perimeter regions of the overlay adjacent the outer edges of the elongated perimeter regions. The platform may include a fixed shroud mounted on the frame structure adjacent the elongated sides of the elongated slidable cradle. The lower surface of each of the elongated ridges may be proximate to the fixed shroud.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

Figure 1:
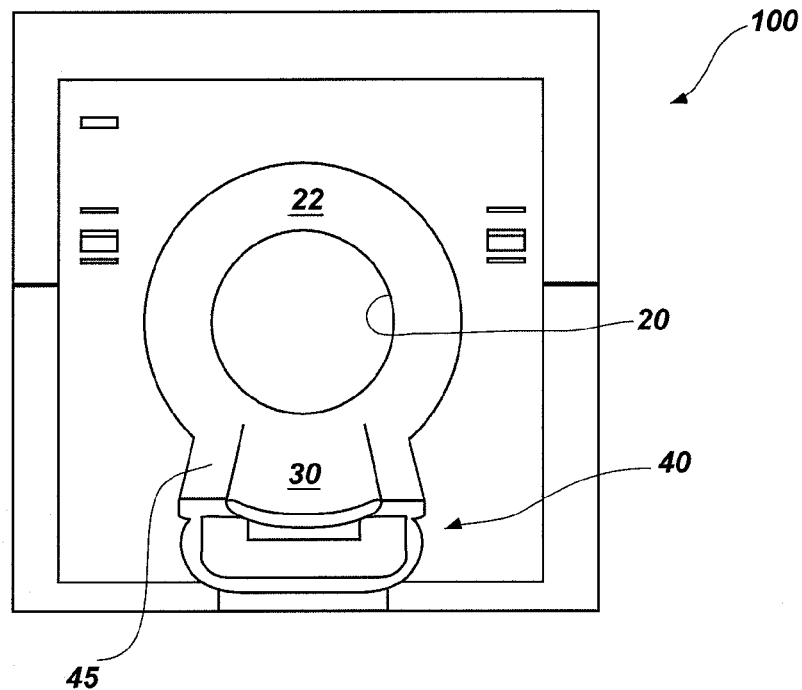
FIG. 1 illustrates a conventional CT scanner.
Figure 2:
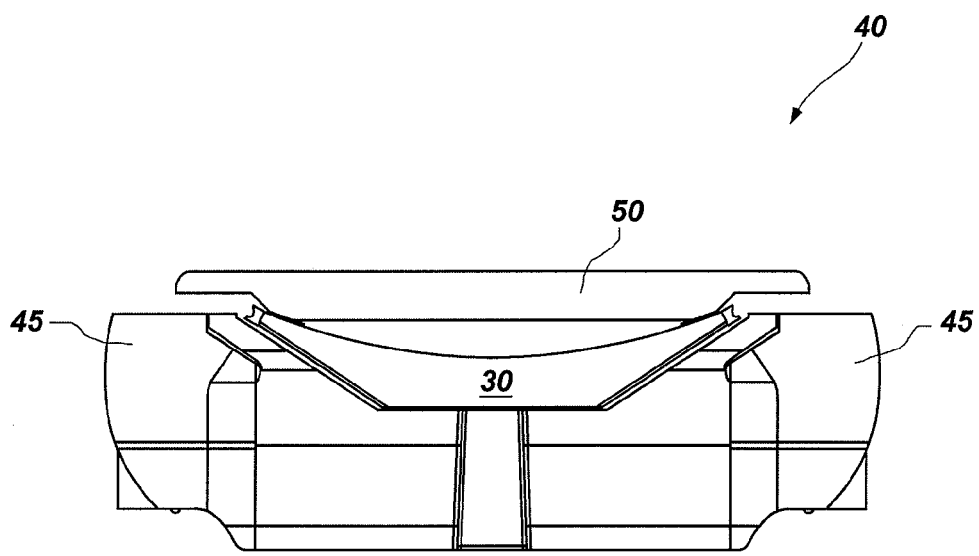
FIG. 2 illustrates a prior art imaging platform.
Figure 3:
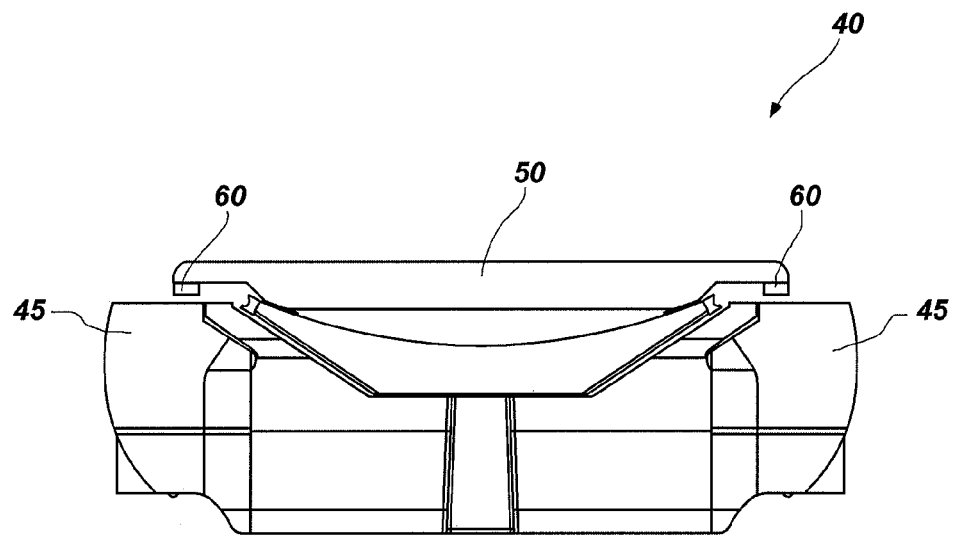
FIG. 3 illustrates another prior art imaging platform.

Although the foregoing description contains many specifics, these should not be construed as limiting the scope of the present invention, but merely as providing illustrations of some representative embodiments. Similarly, other embodiments of the invention may be devised that do not depart from the spirit or scope of the present invention. Features from different embodiments may be employed in combination.

According to embodiments of the invention, an inventive overlay may be configured for mounting on a slidable cradle of a stationary imaging platform. The stationary imaging platform may include a fixed shroud adjacent both sides of the slidable cradle. The inventive overlay may move with the slidable cradle. Elongated perimeter regions of the inventive overlay may have ridges formed on the underside thereof adjacent the outer edges of the elongated perimeter regions. The ridges may serve to prevent objects from becoming pinched between the inventive overlay and the fixed shroud.

Other embodiments of the invention include an elongated overlay having a width, length, and structural integrity to support a human body. The elongated overlay may include a middle region and two elongated perimeter regions formed on opposing edges of the middle region. The elongated perimeter regions may be thinner than the middle region. Elongated ridges may be located on the underside of the elongated perimeter regions adjacent outer edges of the elongated perimeter regions. The underside of the elongated overlay is sized and adapted to interact with another structure. The upper surfaces of the middle region and of the two elongated perimeter regions together may form a common flat surface. The elongated ridges attached to the underside of the elongated perimeter regions may be integrally formed with the underside of the elongated perimeter regions. The elongated ridges may be comprised of a foam or a solid phenolic material.

Embodiments of the invention include an imaging platform. The imaging platform may include a frame structure sized and configured to support a slidable cradle. The slidable cradle may be configured for slidable attachment to the frame structure. A fixed shroud may be attached to the frame structure. The fixed shroud may be formed adjacent opposing sides of the slidable cradle. The imaging platform may include an overlay, sized and adapted to support a human body. The overlay may be detachably mounted on the slidable cradle. The overlay may include elongated perimeter regions having elongated ridges formed on the underside thereof. The lower surface of a middle region of the overlay may be configured to mate with a semi-tubular top surface of the slidable cradle. The underside of the elongated perimeter regions may be configured to avoid contact with the slidable cradle. The overlay may include an elongated upper flat surface, sized and adapted to support a human body.

Embodiments of the invention may include an imaging device. The imaging device may include a rotatable gantry and a platform. The platform may include a frame structure. The platform may also include an overlay, sized and adapted to support a human body, detachably mounted on an elongated slidable cradle. The overlay and the elongated slidable cradle may be configured to slide in and out of the rotatable gantry via the frame structure. The elongated ridges may be formed on underlying elongated perimeter regions of the overlay adjacent the outer edges of the elongated perimeter regions. The platform may include a fixed shroud mounted on the frame structure adjacent the elongated sides of the elongated slidable cradle. The lower surface of each of the elongated ridges may be proximate to the fixed shroud.

Regarding the elongated ridges, the elongated ridges may be comprised of a material compatible with imaging technology utilized by the rotatable gantry. The distance between the outer surface of each of the elongated ridges and the inner surface of the rotatable gantry, when the overlay is in the rotatable gantry, may be less than about 0.35 inch. The distance between the outer surface of each of the elongated ridges and the rotatable gantry, when the overlay is in the rotatable gantry, may be greater than about 1 inch.

Further regarding the elongated ridges, the elongated ridges may have an isosceles trapezoidal cross-sectional shape. The base of each of the elongated ridges may be contiguous with the underside of the elongated perimeter regions. The peak of each of the elongated ridges may include a flat surface parallel to the underside of the elongated perimeter regions. The edges may be rounded where the sides of each of the elongated ridges meet their respective peaks. The peaks of the elongated ridges may be the lowest surface of the elongated ridges. The distance between the peaks and an upper surface of the fixed shroud may be either less than about 0.35 inch or greater than about 1 inch. The sides of each of the elongated ridges may include an outer side and an inner side per elongated ridge. The inner side and the outer side may have equal lengths. The outer side of each of the elongated ridges may abut the outer edge of the underside of the elongated perimeter regions. The inner side of each of the elongated ridges may be located and configured to avoid contact with the slidable cradle.

Figure 4:
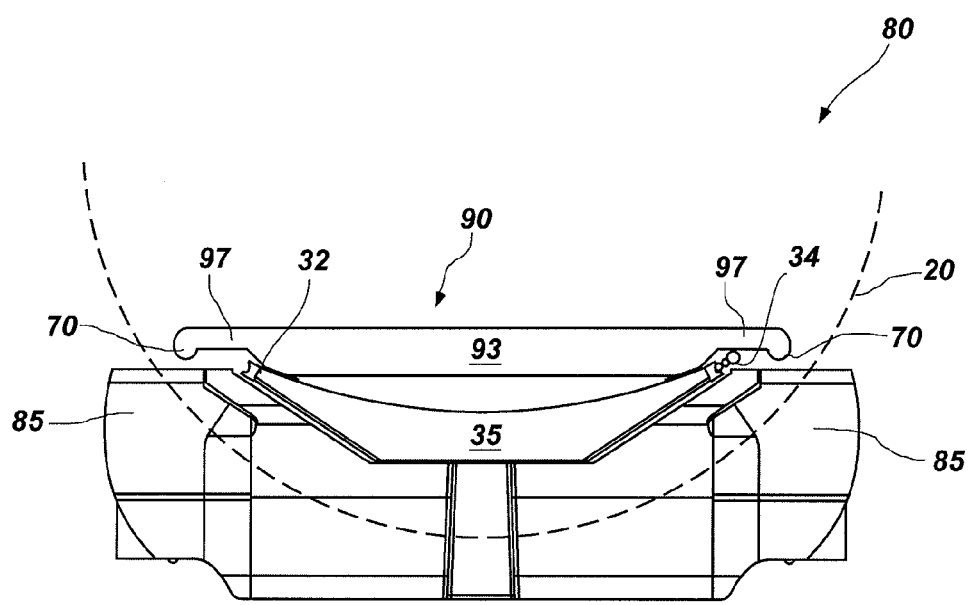
FIG. 4 illustrates an embodiment of an inventive overlay for use with the cradle of an imaging platform.

FIG. 4 illustrates one embodiment of a stationary imaging platform 80. Stationary imaging platform 80 includes cradle 35 and fixed shroud 85 adjacent both sides of cradle 35. Elongated overlay 90 may be configured for mounting on cradle 35. Elongated overlay 90 may have the width, length, and structural integrity to support a human body. Elongated overlay 90 may be configured to move with cradle 35 without contacting either side of fixed shroud 85. Elongated ridges 70 may be formed along the underside of elongated overlay 90 adjacent the outer edges of elongated perimeter regions 97.

Elongated ridges 70 may be made from materials that are durable and/or easily cleanable and sterilizable. For example, elongated ridges 70 may include non-porous materials that do not readily absorb liquids. Elongated ridges 70 may include materials that will not interfere with the CT scan. For a material to not interfere with the CT scan, the material needs to substantially not interfere with x-ray detection. Carbon fiber, for example, is substantially not present radiographically. Additionally, it may also be desirable to keep the weight of elongated overlay 90 to a minimum, thus the materials of elongated ridges 70 may include relatively light-weight materials. It may be desirable to form elongated ridges 70 from a material that is machinable and/or moldable. By way of non-limiting example, elongated ridges 70 may be made from a foam or a solid phenolic material.

In one embodiment, elongated ridges 70 may be integrally formed with elongated overlay 90 during the fabrication of elongated overlay 90. For example, elongated overlay 90 may have a foam core surrounded by a carbon fiber wrap. The carbon fiber wrap may be encased in a solid phenolic material to form the outer surfaces of elongated overlay 90. Elongated ridges 70 may then be formed during the encasing of the carbon fiber. In an alternative embodiment, elongated ridges 70 may be formed separate from elongated overlay 90 and then later secured to the underside of elongated perimeter regions 97 of elongated overlay 90, such as with an adhesive (e.g., an epoxy). Methods of forming and/or machining materials, such as foams or solid phenolic materials, are known in the art, and, therefore, are not discussed in more detail herein.

In one embodiment, elongated ridges 70 extend continuously along the full length of elongated overlay 90. Elongated overlay 90 may extend along the full length of cradle 35. Non-limiting examples of the length of elongated overlay 90, and thus the length of elongated ridges 70, are from about 670 inches (about 1700 cm) to about 866 inches (about 2200 cm). In another embodiment, elongated ridges 70 may extend intermittently along the length of elongated overlay 90. For example, gaps in elongated ridges 70 could be provided along the length of elongated overlay 90 to provide space for restraining straps used to immobilize a patient on elongated overlay 90.

The height (i.e., vertical thickness) of elongated ridges 70 may be determined by the space between fixed shroud 85 and elongated overlay 90 when elongated ridges 70 are not present. In one embodiment, it is desirable that the space between fixed shroud 85 and elongated overlay 90 be either less than about 0.35 inch (about 9 mm) or greater than about 1 inch (about 25 mm) to reduce the probability of an object, such as a patient's finger, from becoming pinched. For example if the distance between each underside of each elongated perimeter region 97 and fixed shroud 85 is about 0.8 inch (about 20 mm), then the height of elongated ridges 70 would need to be about 0.43 inch (about 11 mm) or more. It should be understood that the height of elongated ridges 70 should not exceed the available space between the underside of each elongated perimeter region 97 and fixed shroud 85, so that elongated overlay 90 may not be in contact with fixed shroud 85. Thus, elongated overlay 90 is not restricted from movement with cradle 35.

The width of elongated ridges 70 may be governed by the desired cross-sectional shape of elongated ridges 70 in conjunction with the desired height. For example, when the desired cross-sectional shape of elongated ridges 70 is a hemisphere, then the width of elongated ridges 70 may be twice the height. Or, when the desired cross-sectional shape is an equilateral triangle, then the width may be about 1.15 times the height. However, there may be constraints on the width of elongated ridges 70 as will be discussed below.

FIG. 4 illustrates that elongated overlay 90 may include middle region 93 and elongated perimeter regions 97 on both sides of middle region 93. The upper surfaces of the middle region 93 and of the two elongated perimeter regions 97 may share a common flat surface. Middle region 93 may be thicker than elongated perimeter regions 97. One reason for reducing the thickness of elongated perimeter regions 97 may be to limit the weight of elongated overlay 90. Another reason is that cradle 35 may includes clips 32 and also clip extensions 34.

Clips 32 and clip extensions 34 may limit the width of elongated ridges 70. In one embodiment, the width of elongated ridges 70 may not be so wide as to touch clips 32 and clip extensions 34. Gantry 22 may also place a constraint on the width of elongated ridges 70. Opening 20 (FIG. 4) of gantry 22 for receiving cradle 35 and elongated overlay 90 may be from about 24 inches (about 60 cm) to about 28 inches (about 70 cm). It may be desirable to have a space between elongated overlay 90 and gantry 22 of greater than about 1 inch (about 25 mm) or less than about 0.35 inch (about 9 mm) to reduce the probability of an object, such as a patient's finger, from becoming pinched. Thus, in one embodiment, the width of elongated ridges 70 may not be so wide so as to create a space between elongated overlay 90 and gantry 22 that is less than about 1 inch (about 25 mm) and greater than about 0.35 inch (about 9 mm).

Clips 32 and clip extensions 34 may limit the width of elongated ridges 70. In one embodiment, the width of elongated ridges 70 may not be so wide as to touch clips 32 and clip extensions 34. Gantry 20 may also place a constraint on the width of elongated ridges 70. Opening 22 (FIG. 4) of gantry 20 for receiving cradle 35 and elongated overlay 90 may be from about 24 inches (about 60 cm) to about 28 inches (about 70 cm). It may be desirable to have a space between elongated overlay 90 and gantry 20 of greater than about 1 inch (about 25 mm) or less than about 0.35 inch (about 9 mm) to reduce the probability of an object, such as a patient's finger, from becoming pinched. Thus, in one embodiment, the width of elongated ridges 70 may not be so wide so as to create a space between elongated overlay 90 and gantry 20 that is less than about 1 inch (about 25 mm) and greater than about 0.35 inch (about 9 mm).

Figure 5:
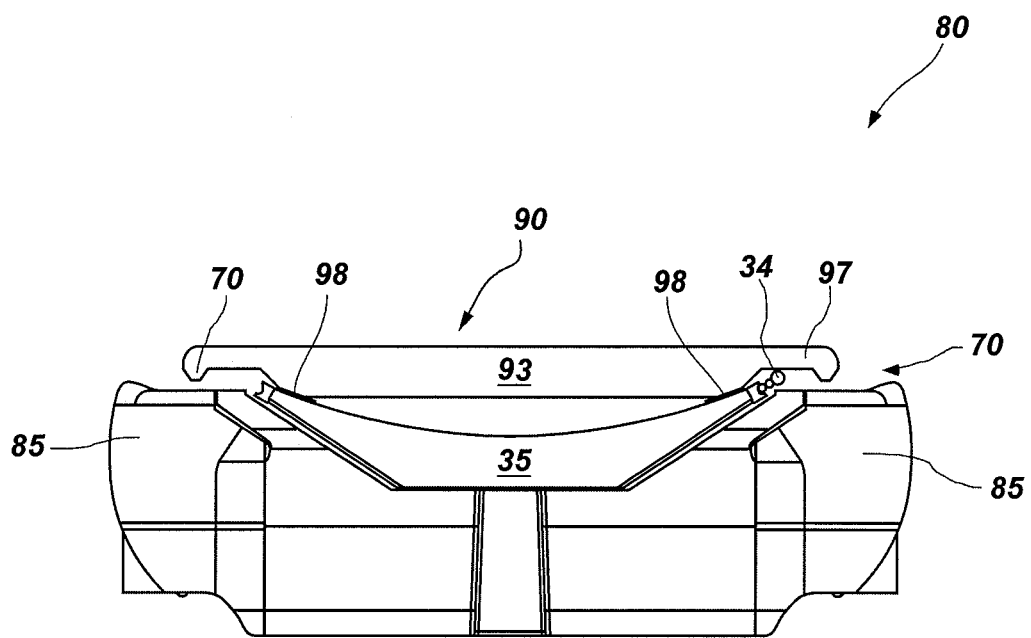
FIG. 5 illustrates another embodiment of an inventive overlay for use with the cradle of an imaging platform.

Elongated ridges 70 may have a variety of cross-sectional shapes. FIG. 5 illustrates an embodiment of the present invention where elongated ridges 70 have an isosceles trapezoid cross-sectional shape. In this embodiment, the sides of elongated ridges 70 are at about a 45 degree angle relative to the underside of elongated perimeter regions 97. In this embodiment, the distance between the "peaks" of elongated ridges 70 and fixed shroud 85 is about 0.3217 inches (about 8.2 mm). Thus, elongated ridges 70 may serve as anti-pinch point devices to limit the space between elongated overlay 90 and fixed shroud 85.

There is no limitation on the shape of elongated ridges 70. However, it may be desirable to use rounded corners, rather than sharp corners, with elongated ridges 70. For example, with the trapezoidal elongated ridges 70 depicted in FIG. 5 it may be desirable to round the corners of the trapezoid. In that example, elongated ridges 70 could still have a trapezoidal shape, but just with rounded corners.

Elongated ridges 70 may thus serve as anti-pinch point devices for elongated overlay 90. Elongated ridges 70 may serve to prevent not only fingers from becoming pinched, but also surgical tubing, blankets, clothing, and numerous other articles.

Elongated overlay 90 may be adapted to interact with another structure. For example, elongated overlay 90 may be mounted on cradle 35 in any manner compatible with elongated overlay 90 moving with cradle 35 in and out of gantry 22. FIG. 5 illustrates that cradle 35 and elongated overlay 90 may include complementary Velcro strips 98 to assist in both securing elongated overlay 90 to cradle 35 and to also cushion the contact between cradle 35 and elongated overlay 90. In the embodiment illustrated in FIG. 5, only a portion of the lower surface of middle region 93 is configured to interact with cradle 35. However, the lower surface of elongated overlay 90 may be configured in any manner necessary to mate with cradle 35. FIGS. 4 and 5 depict the top surface of cradle 35 as having a semi-tubular shape. However, cradle 35 may have any other shape compatible with its function. The lower surface of elongated overlay 90 may be configured to mate with any shape of cradle 35.

Elongated overlay 90 has been described as having a flat upper surface. However, it should be understood that elongated ridges 70 may be used with a variety of CT scanner overlays. For example, the upper surface of elongated overlay 90 may be padded and/or have a curvilinear surface. Additionally, elongated overlay 90 may be an immobilization chamber for immobilizing a patient's head, chest, abdomen, or limbs. For example, the immobilization chamber may be mounted on cradle 35 and have support structures that create pinch points between the immobilization chamber and fixed shroud 85. Embodiments of the present invention may be used to avoid such pinch points.

It should be understood that elongated ridges 70 may be used with any imaging technology that involves a platform having an overlay on a sliding element and a fixed shroud. There are numerous varieties of CT scanners that may use an overlay on a sliding element. Slice CT scanners and volume CT scanners are two non-limiting examples. In addition to CT scanners, other imaging technologies utilize platforms having overlays on sliding elements. For example, magnetic resonance imaging ("MRI"), positron emission tomography ("PET") scanners, positron emission tomography computer tomography ("PETCT") scanners, and linear accelerators may utilize platforms with an overlay on a sliding element and a fixed shroud. The materials of elongated ridges 70 and elongated overlay 90 may need to be varied depending upon the imaging technology used. For example, for MRI, it may be necessary to use materials that do not have magnetic properties.

Although the foregoing description contains many specifics, these are not to be construed as limiting the scope of the present invention, but merely as providing certain representative embodiments. Similarly, other embodiments of the invention can be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. An elongated imaging platform overlay having a width, length, and structural integrity adapted to fit upon a CT-type imaging cradle and to support a human body, comprising:
    a platform having a middle region and two elongated perimeter regions formed on opposing edges of the middle region, wherein the elongated perimeter regions are thinner than the middle region; and
    elongated ridges located on an underside of the elongated perimeter regions adjacent outer edges of the elongated perimeter regions, and wherein an underside of the elongated overlay is sized and adapted to interact with another structure; and
    wherein the overlay further comprises:
        a lower surface of a middle region of the overlay configured to mate with a top surface of the CT-type imaging cradle;
        wherein the elongated ridges have at least one of an isosceles trapezoidal and a hemispherical cross-sectional shape, wherein peaks of the elongated ridges are a lowest surface of the elongated ridges, wherein a distance between the peaks and an upper surface of the another structure is either less than about 0.35 inch or greater than about 1 inch, wherein an inner side of each of the elongated ridges is located and configured to avoid contact with the CT-type imaging cradle; and
        wherein the overlay comprises an elongated upper surface, sized and adapted to support a human body.

2. The elongated overlay of claim 1, wherein upper surfaces of the middle region and of the two elongated perimeter regions together comprise a common flat surface.

3. The elongated overlay of claim 1, wherein the elongated ridges attached to the underside of the elongated perimeter regions comprise elongated ridges integrally formed with the underside of the elongated perimeter regions.

4. The elongated overlay of claim 1, wherein the elongated ridges are comprised of a foam or a solid phenolic material.

5. The elongated overlay of claim 1, wherein a distance between the lower surface of the elongated ridges and an upper surface of the another structure is about 0.3217inches.

6. The elongated overlay of claim 1, wherein the sides of the elongated ridges are at about a 45 degree angle relative to the underside of the elongated perimeter regions.

7. The elongated overlay of claim 1, wherein the elongated ridges extend intermittently along a length of the overlay.

8. An imaging platform comprising:
    a frame structure sized and configured to support a slidable cradle;
    the slidable cradle configured for slidable attachment to the frame structure;
    a fixed shroud attached to the frame structure and formed adjacent opposing sides of the slidable cradle; and
    an overlay, sized and adapted to support a human body, wherein the overlay is sized and structured to detachably mount on the slidable cradle, wherein the overlay comprises elongated perimeter regions having elongated ridges formed on an underside thereof; and
    wherein the overlay further comprises:
        a lower surface of a middle region of the overlay configured to mate with a semi-tubular top surface of the slidable cradle;
        wherein the elongated ridges have an isosceles trapezoidal cross-sectional shape, wherein a base of each of the elongated ridges is contiguous with the underside of the elongated perimeter regions and a peak of each of the elongated ridges includes a flat surface parallel to the underside of the elongated perimeter regions, wherein the edges are rounded where sides of each of the elongated ridges meet the peaks, wherein the peaks of the elongated ridges are the lowest surface of the elongated ridges, wherein a distance between the peaks and an upper surface of the fixed shroud is either less than about 0.35 inch or greater than about 1 inch, wherein the sides of each of the elongated ridges includes an outer side and an inner side per elongated ridge, wherein the inner side and the outer side have equal lengths, wherein the outer side of each of the elongated ridges abuts the outer edge of the underside of the elongated perimeter regions, wherein the inner side of each of the elongated ridges is located and configured to avoid contact with the slidable cradle;
        wherein the underside of the elongated perimeter regions is configured to avoid contact with the slidable cradle; and
        wherein the overlay comprises an elongated upper flat surface, sized and adapted to support a human body.

9. The imaging platform of claim 8, wherein a distance between the lower surface of the elongated ridges and an upper surface of the fixed shroud is about 0.3217 inches.

10. The imaging platform of claim 8, wherein the sides of the elongated ridges are at about a 45 degree angle relative to the underside of the elongated perimeter regions.

11. The imaging platform of claim 8, wherein upper surfaces of the middle region and of the two elongated perimeter regions together comprise a common flat surface.

12. The imaging platform of claim 8, wherein the elongated ridges attached to the underside of the elongated perimeter regions comprise elongated ridges integrally formed with the underside of the elongated perimeter regions.

13. The imaging platform of claim 8, wherein the elongated ridges are comprised of a foam or a solid phenolic material.

14. The imaging platform of claim 8, wherein the elongated ridges extend intermittently along a length of the overlay.

15. An imaging device comprising:
    a rotatable gantry; and
    a platform comprising:
        a frame structure;
        an overlay, sized and adapted to support a human body, detachably mounted on an elongated slidable cradle, wherein the overlay and the elongated slidable cradle are configured to slide in and out of the rotatable gantry via the frame structure, wherein elongated ridges are formed on underlying elongated perimeter regions of the overlay adjacent outer edges of the elongated perimeter regions of the overlay;

a fixed shroud mounted on the frame structure adjacent elongated sides of the elongated slidable cradle, wherein a lower surface of each of the elongated ridges is proximate to the fixed shroud; and wherein the elongated ridges of the overlay have arcuate or angled sides adjacent a central peak, wherein the peaks of the elongated ridges are the lowest surface of the elongated ridges, wherein a distance between the peaks and an upper surface of the fixed shroud is either less than about 0.35 inch or greater than about 1 inch.

16. The imaging device of claim 15, wherein the elongated ridges are comprised of a material compatible with imaging technology utilized by the rotatable gantry.

17. The imaging device of claim 15, wherein a distance between the lower surface of the elongated ridges and an upper surface of the fixed shroud is about 0.3217 inches.

18. The imaging device of claim 15, wherein the sides of the elongated ridges are at about a 45 degree angle relative to the underside of the elongated perimeter regions.

19. The imaging device of claim 15, wherein upper surfaces of the middle region and of the two elongated perimeter regions together comprise a common flat surface.

20. The imaging device of claim 15, wherein the elongated ridges attached to the underside of the elongated perimeter regions comprise elongated ridges integrally formed with the underside of the elongated perimeter regions.

21. The imaging device of claim 15, wherein the elongated ridges are comprised of a foam or a solid phenolic material.

22. The imaging device of claim 15, wherein the elongated ridges extend intermittently along a length of the overlay.

* * * * *

UNITED STATES PATENT AND TRADEMARK OFFICE
CERTIFICATE OF CORRECTION

PATENT NO. : 7,650,657 B2  
APPLICATION NO. : 12/101070  
DATED : January 26, 2010  
INVENTOR(S) : Glenn N. Waterman Page 1 of 1

It is certified that error appears in the above-identified patent and that said Letters Patent is hereby corrected as shown below:

COLUMN 7, LINE 59, change "0.3217inches." to --0.3217 inches.--

Signed and Sealed this
First Day of March, 2011

David J. Kappos
*Director of the United States Patent and Trademark Office*